United States Patent [19]

Koontz

[11] Patent Number: 5,798,261
[45] Date of Patent: Aug. 25, 1998

[54] DISTRIBUTED PORE CHEMISTRY IN POROUS ORGANIC POLYMERS

[75] Inventor: Steven L. Koontz, Houston, Tex.

[73] Assignee: The United States of America as represented by the Administrator of the National Aeronautics and Space Administration, Washington, D.C.

[21] Appl. No.: 254,361

[22] Filed: Jun. 3, 1994

Related U.S. Application Data

[63] Continuation-in-part of Ser. No. 857,901, Mar. 26, 1992, Pat. No. 5,369,012, and a continuation-in-part of Ser. No. 997,265, Feb. 23, 1993, Pat. No. 5,332,551, which is a division of Ser. No. 894,505, Jun. 2, 1992, Pat. No. 5,215,790, which is a division of Ser. No. 429,739, Oct. 31, 1989, Pat. No. 5,141,806.

[51] Int. Cl.$^6$ .............. C12M 1/12; C12N 11/08
[52] U.S. Cl. .............. 435/283.1; 435/180; 435/240.243; 435/297.1; 435/297.5; 435/299.1; 435/299.2; 427/569; 521/27; 210/500.27; 210/500.36
[58] Field of Search .............. 435/240.241, 240, 435/242, 284, 285, 311, 180–182, 283.1, 287.9, 297.1, 297.5, 299.1, 299.2; 210/500.1, 500.21, 500.22, 500.27, 500.36; 427/2.24, 2.3, 2.31, 487, 488, 495, 569; 521/27, 31, 51

[56] References Cited

U.S. PATENT DOCUMENTS

| | | | |
|---|---|---|---|
| 3,702,973 | 11/1972 | Daugherty et al. | 331/94.5 PE |
| 3,826,226 | 7/1974 | Clark | 118/49.1 |
| 3,864,250 | 2/1975 | Perry | 210/31 C |
| 3,904,366 | 9/1975 | Grasenick | 23/230 PC |
| 4,143,949 | 3/1979 | Chen | 351/160 H |
| 4,268,711 | 5/1981 | Gurev | 136/256 |
| 4,346,142 | 8/1982 | Lazear . | |
| 4,362,632 | 12/1982 | Jocob | 422/183.04 |
| 4,394,457 | 7/1983 | Ogasa . | |
| 4,544,485 | 10/1985 | Pinkerton et al. | 210/502.1 |
| 4,560,599 | 12/1985 | Regen . | |
| 4,583,492 | 4/1986 | Cowher et al. | 118/723 |
| 4,608,063 | 8/1986 | Kurokawa | 55/208 |
| 4,619,897 | 10/1986 | Hato et al. | 435/182 |
| 4,686,113 | 8/1987 | Delfino et al. | 427/45.1 |
| 4,756,794 | 7/1988 | Yoder | 156/643 |
| 4,786,603 | 11/1988 | Wielinger et al. | 436/69 |

(List continued on next page.)

OTHER PUBLICATIONS

WPIDS Abstract No. 87–293088 Abstract of Patent DE 3712491 (Sep. 22, 1993).

Tsai, Chi–Chun et al., "Enhanced Albumin Affinity of Silicone Rubber," *Transactions of the American Society of Artificial Organs Internal Organs* (ASAIO), vol. XXXIV, pp. 559–563(1988).

Tsai, Chi–Chun et al., "Biocompatible Coatings with High Albumin Affinity," *Transactions of the American Society of Artificial Organs Internal Organs* (ASAIO), vol. XXXVI, pp. M307–M310 (1990).

(List continued on next page.)

*Primary Examiner*—William H. Beisner
*Attorney, Agent, or Firm*—Hardie R. Barr

[57] ABSTRACT

A method for making a biocompatible polymer article using a uniform atomic oxygen treatment is disclosed. The substrate may be subsequently optionally grated with a compatibilizing compound. Compatibilizing compounds may include proteins, phosphorylcholine groups, platelet adhesion preventing polymers, albumin adhesion promoters, and the like. The compatibilized substrate may also have a living cell layer adhered thereto. The atomic oxygen is preferably produced by a flowing afterglow microwave discharge, wherein the substrate resides in a sidearm out of the plasma. Also, methods for culturing cells for various purposes using the various membranes are disclosed as well. Also disclosed are porous organic polymers having a distributed pore chemistry (DPC) comprising hydrophilic and hydrophobic regions, and a method for making the DPC by exposing the polymer to atomic oxygen wherein the rate of hydrophilization is greater than the rate of mass loss.

37 Claims, 1 Drawing Sheet

U.S. PATENT DOCUMENTS

| | | |
|---|---|---|
| 4,794,002 | 12/1988 | Henis et al. |
| 4,851,121 | 7/1989 | Yokota et al. |
| 4,885,077 | 12/1989 | Karakelle et al. |
| 4,885,086 | 12/1989 | Miura. |
| 4,919,659 | 4/1990 | Horbett et al. |
| 5,026,650 | 6/1991 | Schwarz et al. ............... 435/286 |
| 5,028,453 | 7/1991 | Jeffrey et al. ................. 427/42 |
| 5,098,569 | 3/1992 | Stedronsky. |
| 5,104,729 | 4/1992 | Stedronsky. |
| 5,139,881 | 8/1992 | Henis et al. |
| 5,141,806 | 8/1992 | Koontz ....................... 428/315.5 |
| 5,209,849 | 5/1993 | Hu et al. |
| 5,215,790 | 6/1993 | Koontz ......................... 427/535 |
| 5,282,965 | 2/1994 | Urairi et al. ............... 210/500.36 |
| 5,332,551 | 7/1994 | Koontz et al. ................ 422/129 |
| 5,356,936 | 10/1994 | Howell et al. ................. 521/27 |
| 5,369,012 | 11/1994 | Koontz et al. ................ 435/7.92 |
| 5,384,042 | 1/1995 | Afeyan et al. |
| 5,510,195 | 4/1996 | Sano et al. |

OTHER PUBLICATIONS

C. Stimpson et al., "Patency and Durability of Small Diameter Silicone Rubber Vascular Prosthesis," *Biomaterials, Artificial Cells, and Artificial Organs*, 17(1), (1989), pp. 31–43.

Durrani et al., "Modification of Polymer Surfaces for Biomedical Applications," *Polymer Surfaces and Interfaces*, Chapter 10, J. Wiley and Sons, (1987), pp. 189–200.

Rajender Sipehia, "FTIR–ATR Spectra of Protein A Immobilized on to Functionalized Polypropylene Membranes of Gaseous Plasma of Oxygen and of Anhydrous Ammonia," *Biomaterials, Artificial Cells, and Artificial Organs*, 16(5), (1988–1989), pp. 955–966.

Rajender Sipehia, "The Enhanced Attachment and Growth of Endothelial Cells on Anhydrous Ammonia Gaseous Plasma Modified Surfaces of Polystyrene and Poly(Tetrafluoroethylene)," *Biomaterials, Artificial Cells, and Artificial Organs*, 18(3), (1990), pp. 437–446.

Elizabeth G. Nabel et al., "Recombinant Gene Expression in Vivo Within Endothelial Cells of the Arterial Wall," *Science*, vol. 244, 16 Jun. 1989, pp. 1342–1345.

Hiroo Iwata et al., "Preparation and Properties of Novel Environment–Sensitive Membranes Prepared by Graft Polymerization onto a Porous Membrane," *Journal of Membrane Science*, vol. 38, (1988), pp. 185–199.

J. Wolff, "Tailoring of Ultrafiltration Membranes by Plasma Treatment and Their Application for the Desalination and Concentration of Water–Soluble Organic Substances," *Journal of Membrane Science*, vol. 36, (1988), pp. 207–214.

F. Vigo et al., "Poly (Vinyl Chloride) Ultrafiltration Membranes Modified by High Frequency Discharge Treatment," *Journal of Membrane Science*, vol. 36, (1988), pp. 187–199.

F. F. Stengaard, "Preparation of Asymmetric Microfiltration Membranes and Modification of Their Properties by Chemical Treatment," *Journal of Membrane Science*, vol. 36, (1988), pp. 257–275.

Fang Yuee et al., "Polypropylene Dialysis Membrane Prepared by Cobalt–60 Gamma–Radiation–Induced Graft Copolymerization," *Journal of Membrane Science*, vol. 39, (1988), pp. 1–9.

H. K. Yasuda et al., "Plasma–Surface Interactions in the Plasma Modification of Polymer Surfaces," *Polymer Sciences and Interfaces*, Chapter 8, J. Wiley and Sons, 1987, pp. 149–162.

Attar S. Chawla, "Use of Plasma Polymerization for preparing Silicone–Coated Membranes for Possible Use in Blood Oxygenators," *Artificial Organs*, vol. 3(1), (1979), pp. 92–96.

Y. Ikada, "Development of a Polymer Surface with Non–Adherent Platelet Properties," *Polymers in Medicine and Surgery*, Plastics and Rubber Institute and Science and Technology Publishers, Homchurch, UK, (1986), pp. 6/1–16/8.

DISTRIBUTED PORE CHEMISTRY IN POROUS ORGANIC POLYMERS

CROSS-REFERENCE TO RELATED APPLICATIONS

This is a continuation-in-part of U.S. Ser. Nos. 07/857,901, filed Mar. 26, 1992, now U.S. Pat. No. 5,369,012, and a continuation-in-part of Ser. No. 07/997,265, filed Feb. 23, 1993, now U.S. Pat. No. 5,332,551 which in turn is a division of U.S. Ser. No. 07/894,505, filed Jun. 2, 1992, now U.S. Pat. No. 5,215,790, which in turn is a division of U.S. Ser. No. 07/429,739, filed Oct. 31, 1989, now U.S. Pat. No. 5,141,806.

ORIGIN OF THE INVENTION

The invention described herein was made by employee(s) of the United States Government and may be manufactured and used by or for the Government of the United States of America for governmental purposes without the payment of any royalties thereon or therefor.

FIELD OF THE INVENTION

This invention relates to porous organic polymer structures having a distributed pore chemistry, and particularly to distributed pore chemistry polymers having adjacent hydrophobic and hydrophilic regions, and preparation of such distributed pore chemistry polymers by surface modification with gas-phase radicals without substantial mass loss.

BACKGROUND OF THE INVENTION

The modification of generally inert solids with gas-phase radicals such as atomic oxygen and hydroxyl radicals is known in the art. In earlier U.S. Pat. Nos. 5,141,806 and 5,215,790, both to Steven L. Koontz, there is disclosed a microporous structure with layered interstitial surface treatments, which is prepared by sequentially subjecting a uniformly pore-surface-treated porous structure to atomic oxygen treatment to remove an outer layer of pore surface treatment to a generally uniform depth within the porous solid, and surface treating the so oxidized region of the porous solid with another surface treating agent. The atomic oxygen/surface treatment steps can be repeated, each successive time to a lesser depth within the porous solid, to produce a microporous structure having multi-layered pore surface chemistries. This structure and preparation methodology are disclosed primarily for use with porous substrate structures which are inert in oxidizing plasmas, such as refractory metal oxides like alumina or silica. The surface treating agents are primarily organic compounds which are reactive with atomic oxygen plasma so they can be removed by exposure thereto.

In U.S. Pat. No. 5,369,012 to Koontz et al a method for making a biocompatible polymer article using a uniform atomic oxygen treatment of a polymer substrate is disclosed. The substrate may be subsequently optionally grafted with a compatibilizing compound, such as proteins, phosphorylcholine groups, platelet adhesion preventing polymers, albumin, adhesion promoters, and the like. The compatibilized substrate may also have a living cell layer adhered thereto. Also disclosed are a vascular prosthesis and other articles made by the biocompatibilizing method as well as methods for using such biocompatibilized articles in a cell mass. In addition, membranes made by the biocompatibilizing method are disclosed, and methods for performing immunodiagnostic testing using the membranes. Also, methods for culturing cells for various purposes using the various membranes are disclosed.

The use of polymeric materials for biomedical implants and in biotechnical manufacture is an advancing art. Plasma discharges have been used to engineer such polymers because surface chemistry can be altered without adversely affecting bulk properties which make polymeric materials useful. However, plasma devices typically do not deliver a uniform concentration of the reactive species. Subject to complex interactions, non-uniform distribution of plasma species may increase manufacturing difficulty and impair quality control.

Silicone rubber has long been used in medical devices such as surgical implants due to desirable properties including gas permeability, pliability, degradation resistance, ease of fabrication and relatively good biocompatibility. However, such materials are not completely inert in the body. Recent methods have been sought to improve its biologic inertness by either surface modification to increase hydrophilicity or bulk modification, i.e. incorporating polar groups into the monomer or prepolymer. Tsai, Chi-Chun et al., in *Transactions of the American Society of Artificial Internal Organs* (ASAIO), vol. XXXIV, (1988) discloses a method for increasing the albumin affinity of silicone rubber. A vinyl-methyl silicone comonomer was hydroxylated and then film coated on a silicone rubber sheet. The OH-coated sheet was grafted with a $C_{16}$ alkyl chain having a terminal acyl group by an esterification reaction catalyzed by 4-dimethylaminopyridine. Albumin adsorption and retention was said to be markedly enhanced for surface OH and $C_{16}$ concentrations as low as 5% reaction yield. Tsai, Chi-Chun et al., in ASAIO, vol. XXXVI, (1990) discloses use of the above albumin adsorbed silicone surfaces as thin transparent, biocompatible films for coating the surfaces of blood contacting devices. These films are said to retard undesired responses, e.g. blood coagulation and activation of complement proteins, platelets and white blood cells, triggered by exposure of blood stream macromolecules to a foreign surface.

Polymer prostheses have been considered for vascular applications. C. Stimpson et al., in *Biomaterials, Artificial Cells, and Artificial Organs*, 17 (1), (1989), pp. 31–43 discloses silicone rubber canine aortic prostheses. A uniformly microporous prosthesis is made by molding the polymer in a template taken from the skeletal structure of a marine life form.

Durrani et al., in *Polymer Surfaces and Interfaces*, chapter 10, J Wiley & Sons, (1987), pages 189–200 discloses modification of polymer surfaces with a phosphorylcholine, for example, to mimic biomembrane surfaces in bioapplications. Modifications of this sort are said to reduce foreign surface induced thromboses associated with the use of blood contacting devices.

Rajender Sipehia in *Biomaterials, Artificial Cells and Artificial Organs*, 16 (5), (1988-89), pp. 955–966 discloses immobilizing proteins to polymeric surfaces. Polypropylene membranes are treated by gaseous oxygen or ammonia plasma to add hydroxyl or amino groups to the polymer surface. The proteins are then grafted to the surface. Rajender Sipehia in *Biomaterials, Artificial Cells, and Artificial Organs*, 18 (3), (1990), pp. 437–446 discloses ammonia plasma modification of polystyrene petri dishes and poly(tetrafluoroethylene) membranes and grafting of proteins to the surface. The growth of bovine pulmonary artery endothelial cells on the modified surface is enhanced by adherence to the grafted proteins.

In U. S. Pat. No. 4,134,949 to Chen, the surface of a contact lens is modified by deposition of a hydrophilic polymer under the influence of plasma glow discharge to integrally bond the coating to the surface of a hydrophobic lens.

Elizabeth G. Nabel et al., in *Science*, vol. 244, 16 Jun. 1989, pp. 1342-1345 discloses a transplant of endothelial cells expressing a recombinant gene into an arterial wall. The transplanted cells may contribute to altering the thrombic properties of the vessel lumen by inducing smooth muscle cell proliferation and regulating smooth muscle cell tone. In addition, genetically altered cells could transmit recombinant DNA products.

Polymer surfaces have been modified by plasma application to prepare membranes for dialysis and ultrafiltration. Hiroo Iwata et al. in *Journal of Membrane Science*, vol. 38, (1988), pp. 185-189 discloses a macroporous poly (vinylidene fluoride) membrane pretreated by air plasma and subsequent graft polymerization of hydrophilic monomers on the treated surface. Such membranes are said to be environment-sensitive and can be used to mimic biological membranes or in a closed-loop drug delivery system. J. Wolff, *Journal of Membrane Science*, vol. 36, (1988), pp. 207-214; F. Vigo et al., *Journal of Membrane Science*, vol. 36, (1988), pp. 187-199; F. F. Stengaard, *Journal of Membrane Science*, vol. 36, (1988), pp. 257-275; and Fang Yuee et al., *Journal of Membrane Science*, vol. 39, (1988), pp. 1-9 disclose the preparation of a variety of dialysis and ultrafiltration membranes.

Various polymers have been modified by plasma processes to alter surface chemistry, adhesion properties, and the like. See H. K. Yasuda et al., *Polymer Surfaces and Interfaces*, chapter 8, J Wiley & Sons, (1987), pages 149-162.

SUMMARY OF THE INVENTION

The present invention is directed to the discovery that certain porous organic polymers which are reactive with plasma radicals have a rate of mass loss which is substantially less than the rate of pore surface modification such that the porous polymers can be effectively treated and made hydrophilic by exposure to atomic oxygen. Exposure of organic-coated inorganic materials (say, silica) to atomic oxygen generally were observed to result in complete removal of the hydrophobic organic coating to leave bare a "clean" hydrophilic silica surface. In view of the distinct reaction fronts between the hydrophobic and hydrophilic interstitial surface region in silica particles treated with atomic oxygen, it was to be expected that the similar treatment of a porous organic polymer (without any inert silica in it) would similarly result in the total or severe mass loss of the reactive, organic polymer without the ability to retain much of the original interstitial surface and porous structure. It was, therefore, quite surprising to discover that porous polymers such as sintered polyethylene (POREX) or porous polyethylene films (CELGARD K-878) could be exposed to atomic oxygen and obtain interstitial surface modification, from hydrophobic to hydrophilic, without substantial loss of the original mass of the polymeric matrix.

The present invention is directed to a distributed pore chemistry in a porous organic polymer and a method for the fabrication thereof. The distributed pore chemistry polymer has porous hydrophobic and hydrophilic regions which have pores interconnected between adjacent regions. The distributed pore chemistry can be obtained, for example, by exposing an exterior surface of the porous polymer substrate to an oxidizing or reducing gas, containing an oxidizing or reducing species such as atomic oxygen, hydroxyl and amino radicals, or the like, at conditions and for a time effective for the radicals to permeate into the pores, react with and hydrophilicize an interstitial surface of the substrate, essentially without significant mass loss.

In one aspect, then, the present invention provides a porous organic polymer having an exterior surface, an interstitial surface and a distributed pore chemistry. The interstitial surface includes interconnected pores formed in the organic polymer which open to the exterior surface. The distributed pore chemistry includes adjacent hydrophobic and hydrophilic regions, wherein the pores in the adjacent regions are interconnected. The hydrophilic region can be formed by surface modification with oxidizing or reducing species selected from atomic oxygen, hydroxyl, amino and like radicals, and can thus be essentially free of leachable surface modification, such as surfactants which have been used in the prior art to obtain hydrophilicity.

The polymer generally has an effective pore diameter of at least about 0.01 microns, preferably at least about 1 micron, and more preferably from about 10 to about 2000 microns. The porous polymer structure is preferably made by sintering particulated polymers which are reactive in the presence of plasma radicals. Alternately, the porous polymer can be made by one of a variety of techniques well known in the art, such as film drawing, or one of a variety of methods conventional in the art, such as described in Kesting, Robert E., *Synthetic Polymeric Membranes*, John Wiley & Sons, New York, pp. 237-309 (1985), which is hereby incorporated herein by reference. Such polymers include, as representative examples, polyethylene, polypropylene, ethylene-vinyl acetate copolymer, polystyrene, styreneacrylamide copolymer or the like, alone or in combination, and optionally including relatively inert materials such as polyvinylidene fluoride, polytetrafluoroethylene, polyalkylsiloxanes or the like. A preferred polymer for preparing the distributed pore chemistry solid is a sintered polyolefin, such as sintered low density polyethylene, high density polyethylene, polypropylene, and the like. The sintered polymers generally have a void volume from about 35 to about 60 percent.

The distributed pore chemistry polymer is preferably obtained by exposing at least a portion of the exterior surface of a hydrophobic polymer substrate to an oxidizing or reducing gas, containing an oxidizing or reducing species selected from atomic oxygen, hydroxyl, amino and like radicals, at conditions and for a period of time effective to hydrophilicize a portion of the interstitial surface to form the hydrophilic region. Preferably, the hydrophilic region formed by the exposure to the oxidizing or reducing gas experiences a mass loss of less than about 10 percent of the region before said exposure, more preferably less than about one percent. If desired, mass loss can be reduced or eliminated while retaining the ability to hydrophilicize a region of a reactive porous polymer by precoating the pore surfaces with a polymeric dihydrocarbylsiloxane which reacts with atomic oxygen or other reactive oxidizing gaseous radicals to produce a hydrophilic silicon oxide which protects the underlying reactive polymer from further oxidation.

In a preferred embodiment, the distributed pore chemistry polymer includes an exterior surface and an interstitial surface comprising interconnected pores, formed in the polymer which have an effective pore diameter from about 0.1 to about 2000 microns. The distributed pore chemistry polymer also includes hydrophobic hydrohydrophilic regions of the interstitial surface, and pores interconnected across a boundary between the hydrophilic and hydrophobic regions. Alternatively, the hydrophilic region may comprise the entire porous polymeric solid. The hydrophilic region is created with gaseous oxidizing or reducing species selected from atomic oxygen, hydroxyl, amino and like radicals. The hydrophilic region is essentially free of leachable surface modification, and has a void fraction less than ten percent greater than a void fraction of the hydrophobic region, more preferably less than 0.25 percent greater.

In another aspect, the present invention provides a method for hydrophilicizing a porous, hydrophobic organic polymer substrate. The method includes the steps of: (a) exposing an interior surface of the substrate to an oxidizing or reducing gas, containing an oxidizing or reducing species such as, for example, atomic oxygen, hydroxyl, amino and like radicals, at conditions and for a time effective to hydrophilicize an interstitial surface of the substrate essentially without mass loss; and (b) recovering a substrate having a hydrophilic interstitial surface to a depth distal from said exterior surface. The mass loss from the interstitial surface exposed to the oxidizing or reducing species is preferably less than 10 percent, more preferably less than 0.25 percent. The exposure is preferably of limited duration to form a distinct reaction front behind which the substrate is hydrophilicized, and in front of which the substrate remains hydrophobic. The recovered substrate desirably has pores interconnected across the reaction front. The substrate can be a sintered polyolefin such as, for example, high density polyethylene, low density polyethylene, polypropylene, and the like. The polymer substrate preferably has an effective pore diameter of at least about 0.1 microns, more preferably at least about 1 micron and especially from about 10 to about 2000 microns. If desired, the resulting polar groups, including alkyl or aryl hydroxyl, ketone, carboxylic acid, or aldehyde groups, formed on the pore surfaces by reaction with atomic oxygen or other gaseous oxidizing agents, are used as reactive sites for subsequent attachment of a variety of organic or biological compounds as described more fully below.

Another method of the present invention is based on the discovery of an atomic oxygen, hydroxyl radical and/or amino radical treatment method capable of producing a substantially uniform concentration of reactive species. Polymer substrates so treated have a uniform distribution of hydrophilic functionality on the treated surface. Such functionality is useful for biocompatibilizing polymer articles for biomedical and biotechnical applications.

In a broader sense, the present invention provides a biotechnical method, comprising the steps of: (a) exposing a hydrophobic exterior polymer surface to a substantially axially uniform dosage of atomic oxygen, hydroxyl or amino radicals at a temperature below about 100° C. sufficient to form a uniform layer of hydrophilic hydroxyl or other polar organic functional groups on said surface, wherein the dosage is generated by a flowing afterglow microwave discharge, wherein the surface is outside of a plasma produced by the discharge; and (b) recovering a biocompatible article. The method may further comprise the steps of grafting a compatibilizing compound to the surface following the exposing step and adhering a layer of living cells to the compatibilizing compound. The grafting step may include the preliminary step of treating the surface with a dihalodialkylsilane coupling agent. The compatibilizing compound is preferably selected from the group consisting of bioactive compounds such as phosphorylcholines, peptide sequences, lipids and proteins; polymers such as poly (ethylene oxide) and poly(vinyl alcohol); and compounds comprising acyl terminated long-chain alkyl radicals. The dosage over the exposed surface preferably comprises a concentration within about 10 percent of an average dosage over the surface and is essentially free of atomic oxygen, hydroxyl or amino dose variation in a radial direction. As one preferred aspect, the method of the invention can be used to vascularize a cell mass wherein a prosthesis is prepared from a polymeric tube having an outside surface biocompatibilized with an adhered layer of cells as described above and then inserting the prosthesis into the cell mass. In general, an implantable article can be prepared by appropriately treating membranes, tubes or molded forms. Another method of the invention can be used to conduct an enzyme-linked immunosorbent assay test. A membrane having a hydrophilic surface and a hydrophobic surface is prepared as described above. Known antibodies are adhered to the hydrophobic surface. Then the hydrophilic surface is placed in contact with an adjacent absorbent material. The antibodies are covered with a test solution, wherein antigens specific to the antibodies adhere thereto to form an antibody-antigen complex and the non-compatible antigens are absorbed by the absorbent material. The hydrophobic surface is covered with a solution of the antibodies conjugated to an indicating enzyme, wherein the conjugated antibodies and the antigen-antibody complex form an antibody-antigen-antibody/enzyme complex and excess fluid is absorbed by the absorbent material. The antibody-antigen-antibody/enzyme complex is developed with a solution of developing compound reactive with the enzyme to indicate presence of the antibody-antigen-antibody/enzyme complex as a positive result or an absence of the complexes as a negative result, wherein excess developing solution is absorbed by the absorbent material.

Further, a method of the invention can be used to culture cells for malignant cell evaluation. A membrane is prepared having a surface comprising a plurality of hydrophilic regions bounded by hydrophobic regions as described above. A group of cells are distributed on the membrane in a growth medium, wherein the cells adhere to the hydrophilic regions at a maximum density of one cell per each hydrophilic region and hydrophobic regions are substantially free of adhered cells. The cells are grown on the membrane and a count of malignant cells growing on the membrane cells is obtained.

Yet another method of the invention can be used to culture cells with enhanced recovery of biological products. A membrane with first and second opposing surfaces is prepared wherein the first surface comprises a hydrophilic area bounded by a hydrophobic area as described above. Cell culturing and product compartments are formed separated by the membrane, wherein the first membrane surface is adjacent the cell culturing compartment and the second membrane surface is adjacent the product compartment, the cell culturing compartment comprising cells in a growth medium, the cells having a gene for the expression of a desired product. The cells are induced to adhere to the hydrophilic area of the first surface of the membrane, wherein the cells polarize with a basal cell wall adjacent the first surface. Nutrient migration is induced from the nutrient compartment to the cells compartment by maintaining nutrient in the cell culturing compartment, wherein the cells absorb the nutrient and in response thereto secrete a product preferentially through the basal cell wall and the membrane into the product compartment.

Yet a further method of the invention can be used to culture cells with self-replenishing nutrients. A membrane is prepared with a first hydrophobic surface and a second hydrophilic surface as described above. A nutrient compartment and a compartment are formed on opposite sides of the membrane, wherein the second surface is adjacent the nutrient compartment and the first surface is adjacent the cells compartment, the nutrient compartment comprising a solution of nutrient and the cells compartment comprising cells in a growth medium. Migration is induced of said nutrient from said nutrient compartment to said cells compartment by maintaining a concentration of said nutrient in said nutrient compartment.

In another embodiment, the invention provides biotechnical polymer articles suitable for use in biomedical or biotechnical applications, comprising at least one surface biocompatibilized at least in part by the method described above. The biocompatibilized surface can comprise a substantially uniform distribution of reactive hydrophilic functionality, a compatibilizing compound grafted to the surface using the hydrophilic functionality and/or a layer of living cells adhered to the surface using the hydrophilic functionality and/or the compatibilizing compounds. Examples of such articles include vascular prostheses, membranes, dressing textiles, molded implants having surfaces inhibiting platelet adhesion and articles having surfaces enhancing cell adhesion.

In a further embodiment, the invention provides a bioreactor comprising a housing; a membrane having at least a portion of one biocompatibilized surface made by the method described above dividing the housing into an opposing nutrient compartment and product compartment; and cells in a growth medium in the nutrient compartment.

In another embodiment, a cell or tissue culture flask comprises a housing and a porous polymer structure mounted in the housing. Cells to be cultured are adherent to a hydrophilic, interstitial surface in the porous polymer structure. A growth medium is in fluid communication with pores interconnected between an exterior surface of the polymer structure and the interstitial surface. The interconnected pores preferably have an effective diameter at least about 5 times the average diameter of the cells as attached to the interstitial surface. The hydrophilic surface in the polymer structure is preferably obtained by exposing an exterior surface of a porous, hydrophobic organic polymer substrate to an oxidizing or reducing gas from a flowing afterglow discharge device, containing an oxidizing or reducing species such as atomic oxygen, hydroxyl, amino and like radicals, at conditions and for a time effective to hydrophilicize an interstitial surface of the substrate, and recovering the polymer structure. The substrate preferably has a rate of mass loss from the interstitial surface exposed to the oxidizing or reducing species substantially less than a rate of hydrophilicization. A compatibilizing compound can be grafted to the hydrophilic, interstitial surface following the exposure step. The compatibilizing compound can be grafted to the surface using a dihalodialkylsilane coupling agent. The compatibilizing compound is, for example, selected from phosphorylcholines, peptides, lipids, proteins, or the like. Or, the compatibilizing compound can be a polyvinyl alcohol, polyethyleneoxide, or the like. The substrate used to prepare the porous polymer structure is preferably polyethylene, polycarbonate, polystyrene, or the like, or a combination thereof. By appropriately treating the porous polymer structure, a modified interstitial surface can be disposed adjacent the cell-adherent surface for selectively retaining a protein secreted from the cells. The modified protein affinity surface can be coupled to a lightly crosslinked gel, for example, dextron, agarose, polyacrylamide, or the like, with attached ligands, having an affinity for the secreted protein. The gel-filled porous polymer structure can be prepared by the exposure to the oxidizing or reducing gas, as mentioned above, to hydrophilicize the interstitial surface to an initial depth spaced from the exterior surface, coupling the gel to the interstitial surface, derivatizing the gel with the protein affinity ligand, crosslinking the gel, and exposing the exterior surface of the substrate to the oxidizing gas to remove the gel to a lesser depth than the initial depth of treatment. This forms a hydrophilicized region from the exterior surface to the lesser depth, and an affinity gel-coupled region from the lesser depth to the initial depth. The porous polymer structure can be a sheet, or more preferably, a plurality of longitudinal, spaced-apart ridges secured to an interior surface of the housing. The housing can be cylindrical with a rectangular transverse cross-section, or in one preferred embodiment, the housing has a circular transverse cross section and the polymer structure is mounted on a longitudinal interior surface of the housing.

DESCRIPTION OF THE INVENTION

Figure 1:
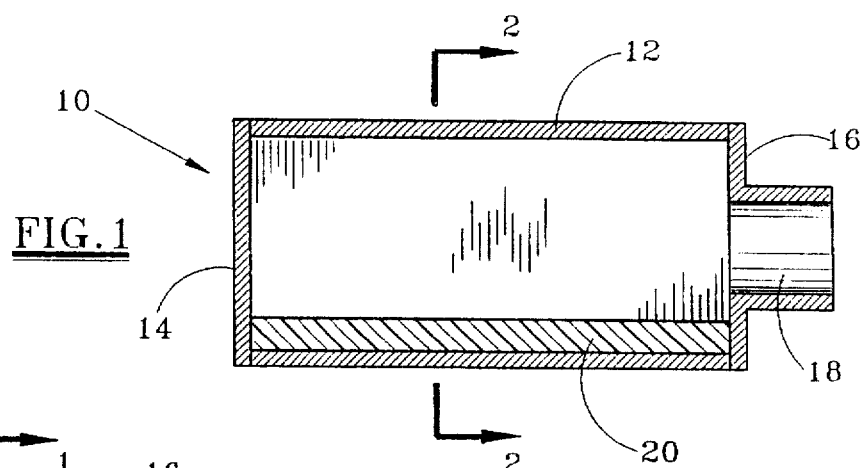
FIG. 1 is a side sectional view of a cell-culturing T-flask according to one embodiment of the present invention.

A substantially uniformly compatibilized polymer article for a biologic environment, i.e. in the presence of bioactive molecules, can be obtained by treating a sufficient amount of surface of the article with a substantially uniform concentration of an oxidizing or reducing plasma species, then optionally grafting compatibilizing compounds to the treated surface. In addition, the grafted substrate may be used as a base for succeeding grafts or as an adhesive layer for proteins or living cells.

In one aspect, a hydrophobic polymer substrate may be treated with a substantially uniform concentration of atomic oxygen, hydroxyl or amino radicals to form a substantially uniform hydrophilic surface layer on the substrate. The hydrophilic surface substantially comprises reactive hydroxyl functionality. A hydrophilic surface may be used to enhance water wettability of the substrate, enhance surface adsorption of proteins or other bioactive compounds, enhance surface adherence of cells or as a base for further surface compatibilizing grafting reactions.

As another aspect, the substantially hydrophobic surface layer may be made to undergo one or more modifications in a series of chemical reactions to graft a compatibilizing compound to the substrate surface. Various kinds of compatibilizing compounds are contemplated and may be used so long as the result is a substrate more compatible with the biologic environment of the application involved. By "compatibilizing," it is meant that an otherwise non-biologic surface, e.g. hydrophobic polymer surface, is made more like known biologic surfaces to a substantial but varying degree.

The compatibilizing compound may be bioactive, i.e. found in life processes, or non-bioactive, but serving to compatibilize the substrate in situ. Representative examples of bioactive compounds which may be used include compounds having phosphoryl-choline functionality, peptides, proteins, lipids, nucleic acids, and the like. Substrates with protein or other bioactive grafts have several compatibilizing applications. One important use is preventing thrombosis around an implanted article by mimicking biologic surfaces. As another use, grafted proteins may serve as an adherent surface or adsorbent for cultured cells.

Other compounds which have been found to have a compatibilizing use include polymeric groups such as poly (vinyl alcohol) and poly(ethylene oxide); and an acyl terminated upper alkyl radical such as an acyl terminated alkyl radical of about 16 carbon atoms. The former have been found to inhibit platelet sticking in the blood stream, see Y. Ikada, "Development of a Polymer Surface with anti-adherent Platelet Properties" compiled in *Polymers in Medicine and Surgery*, Plastics and Rubber Institute Science and Technology Publishers, Hornchurch, UK, 1986 which is hereby incorporated herein by reference. The latter has been found to have enhanced affinity for blood proteins such as albumin. This albumin layer inhibits clotting at the compatibilized surface. See Tsai, Chi-Chun et al., ASAIO, vols. XXXIV (1988) and XXXVI (1990) which are hereby incorporated herein by reference.

As a further aspect, a substrate comprising a protein grafted polymer surface can have living cells such as endothelial cells adhered to the protein grafts. Furthermore, such cells can be genetically altered to transmit recombinant DNA products. Such substrates can be utilized in vascular, skeletal, and the like prostheses; as a vascular network for microgravity cell culturing processes; or in earth-based bioprocessing methodology, e.g. affinity columns. Vascular prostheses can be used in persons suffering advanced arteriosclerosis.

For the compatibilizing surface treatment, highly reactive atomic oxygen or hydroxyl radicals are preferred oxidizing agents, and amino radicals are the preferred reducing agents. Atomic oxygen has the advantage over molecular oxygen of obtaining a distinct oxidation front, generally on the order of a molecular diameter, i.e. from about 50 to about 5000 angstroms. In addition, atomic oxygen does not require the high temperatures that thermal, molecular oxygen requires, so there are no thermally induced changes in the physical or structural characteristics of the polymer when the atomic oxygen is used at a low temperature, preferably below about 100° C., and more preferably below about 40° C.

To obtain uniform treatment of the substrate, a flowing afterglow discharge type atomic oxygen reactor is generally required. The surface of the article to be treated should be out of the plasma and the reactor configured to deliver a relatively uniform dose of oxygen atoms. The specific design of the flowing afterglow device will depend, of course, on the shape of the polymer article using the well known principles of diffusion/reaction kinetics in flowing systems.

To limit oxidation or reduction of the outer portion of the substrate and avoid altering the bulk properties of the polymer, highly reactive atomic oxygen, hydroxyl radicals and amino radicals are the preferred oxidizing and reducing agents, produced in accordance with the apparatus and methodology described in U.S. Pat. Nos. 5,141,806 and 5,215,790 to Koontz which are hereby incorporated herein by reference. Amino radicals are produced by using an ammonia gas in the reactor in place of the oxygen-containing gas used to produce atomic oxygen and/or hydroxyl radicals.

As an intermediate step, a silane coupling agent may be used to graft the compatibilizing compound to the substrate surface. Such silane grafting reactions are known. Generally, the coupling agent comprises a suitable functional group which may be grafted to the substrate surface. The grafted functional group may be made to undergo subsequent chemical reaction with an appropriate compatibilizing compound. Alternatively, the silane coupling agent is attached to the compatibilizing compound first.

One class of suitable silane coupling agents has the formula:

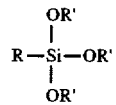

wherein R' independently comprises lower alkyl radicals or hydrogen, R comprises R"—Y wherein R" comprises a lower alkyl radical and Y is selected from the group consisting of terminal amino, mercapto, hydroxy, alkoxy, glycido and carboxy functionality. Representative examples include 3-aminopropyltris-(methoxy)silane, 3-mercaptopropyltris(methoxy)silane, 3-glycidopropyltris (methoxy)silane, 2-carboxyethyltris-(ethoxy)silane, 4-hydroxybutyltris (propyloxy)silane, and the like. Another type silane coupling agent comprises dihalodialkylsilanes. Exemplary is dichlorodimethyl-silane.

In addition, a first coupling agent grafted to the substrate or reacted with the compatibilizing compound may form an intermediate for a reaction with one or more additional coupling agents. Exemplary of such additional coupling compounds is tresyl chloride:

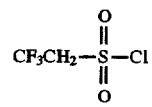

Tresyl chloride reacts with a terminal amino group in a glycine unit of a peptide sequence to couple the sequence to the underlying substrate.

The method of the present invention is suitable for use on most polymer substrates having inert hydrophobic surfaces. Such polymers are either carbon or silicon based. Representative examples of typical carbon-based polymers include polyolefins such as high and low density polyethylene and polypropylene, poly(ethyleneterephthlate), polyimides, polystyrene, polytetrafluoroethylene, poly (vinylidene fluoride), and the like. Examples of suitable silicon-based polymers include polydimethylsiloxane, polyphenylsiloxane, dimethylsiloxane/methylvinylsiloxane copolymer, crosslinked polysiloxanes obtained by hydrosilylation, condensation or free radical crosslinking of siloxane prepolymers or organosiloxane polymer mixtures, and the like.

Substrates may have most commonly known forms including textiles, tubes, films, membranes, sheets, molded forms, as well as composite films, membranes, textiles, and the like with other inert polymeric and non-polymeric materials used for reinforcement. As an example, a breathable, hydrophobic polysiloxane membrane reinforced with poly (tetrafluoroethylene) is sold under the tradename SILON by Bio-Med Sciences, Inc. These membranes are typically used as wound dressings, gas and fluid exchange membranes, etc.

The distributed pore chemistry (DPC) embodiment of the present invention can be obtained by treating a porous organic polymer with the gaseous radicals from the plasma. The polymers suited for treatment in this embodiment are generally reactive with the plasma radicals and will experience mass loss upon exposure to the radicals for a sufficient period of time. However, the polymer and treatment conditions are selected in this embodiment so that the rate of mass loss is relatively low compared to the rate of surface modification with the plasma radicals in the interstitial pores of the polymer matrix. In this manner, the polymer matrix is relatively unchanged by the treatment, and the supporting structure generally retains its bulk and mechanical properties. However, the surface of the pores exposed to the radicals diffusing through the pores reacts with the radicals to become modified by the formation of polar groups as the reaction product between the diffusing radicals and the exposed surface.

As the radicals diffuse through the pores of a hydrophobic polymer, the surfaces of the pores become modified with polar groups and are made hydrophilic. Generally, the diffusion of the radicals from an exterior surface of the polymer proceeds in a distinct front. Behind the front, the interstitial surfaces of the pores become hydrophilic from the addition of polar groups. Ahead of the front, the pore surfaces remain hydrophobic. However, if the reaction front is allowed to pass through the entirety of the polymer material, the bulk material is rendered hydrophilic. The distribution of the pore chemistry between hydrophilic and hydrophobic regions is generally determined by controlling the exposure to the reactive radicals and the shape, direction and distance of the reaction front through the pores.

To further inhibit mass loss, the pore surfaces can be precoated with an organosiloxane, preferably a dihydrocarbylsiloxane such as polydialkylsiloxane or polydiarylsiloxane. Polydimethylsiloxane sold under the trade designation DOW CORNING 704 is a representative example. The siloxane is non-volatile and can be applied in a solvent vehicle, such as hexane, to the porous polymer substrate. The solvent is evaporated, for example in a vacuum oven, to leave the pore surfaces coated with the hydrophobic siloxane. When the substrate is exposed to the oxidizing species, the hydrophobic siloxane reacts to form a hydrophilic silicon oxide coating. The coating is generally inert and serves to protect the underlying reactive polymer from further oxidation by the oxidizing species diffusing the past oxidized surface. In this manner, the rate of mass loss is significantly reduced while at the same time allowing hydrophilicization of the pore surface.

Organic polymer substrates which can be treated according to the present invention to obtain distributed pore chemistry solids are generally porous hydrophobic materials which are reactive with plasma radicals. The polymer matrix structure is preferably permeable, i.e. the pores are interconnected to allow fluid flow from an exterior surface into an adjacent region in the structure, and from one adjacent region to another.

The polymer substrate is characterized by interconnected pores on a larger-than-molecular scale, i.e. the pores generally have effective diameters larger than about 0.01 microns (1 angstrom), preferably at least about 1 micron, and especially from about 10 to about 2000 microns. Thus, the present material can be distinguished from semipermeable solid-phase membranes which generally have interatomic or intermolecular openings on a subatomic scale for molecular diffusion. The porous substrate can have any desired physical shape such as a cube, block, sphere, tube, rod, sheet, or the like.

The polymer in the DPC embodiment can be a synthetic, semisynthetic, or naturally occurring organic polymer, such as, for example, polyamide, polyvinylchloride, polyolefin, polystyrene, polyurethane, polyacrylate, phenolic, alkyd, polyester, cellulose, starch, polysaccharide, polypeptide, rubber, gutta percha, and the like. Polystyrene and polyolefins such as low density polyethylene, high density polyethylene, polypropylene and the like are preferred polymer substrates, especially those manufactured by sintering finely divided polymer particles at an elevated pressure and/or temperature. Sintered polyolefins are available commercially, for example, under the trade designation POREX.

The DPC hydrophilic/hydrophobic porous polymer can be made by exposing an exterior surface of the porous polymer substrate to a source of atomic oxygen, hydroxyl, amino or similar radicals in a particle plasma in much the same manner as the treatment of solid polymer surfaces as described above. Atomic oxygen reactors such as plasma ashers are conventional, for example, but other suitable sources of atomic oxygen include ram flux in low earth orbit, laser photo dissociation, and the like. Oxidation of the interstitial surfaces of the porous polymer structure with highly reactive atomic oxygen has the advantage of obtaining a distinct oxidation reaction front, generally on the order of one effective pore diameter of the structure, a result not possible with less reactive molecular oxygen which does not obtain a sharp reaction front and tends to complete mass loss of combustible organic polymers rather than surface modification. In addition, atomic oxygen does not require the high temperatures that thermal, molecular oxygen requires, so there are no thermally induced changes in the physical or structural characteristics of the porous polymer when atomic oxygen is used at a low temperature, preferably below about 100° C., and more preferably below about 40° C.

The sidearm and drop tower oxygen reactors and general methodology disclosed in U.S. Pat. Nos. 5,141,806 and 5,215,790 are particularly preferred for preparing the DPC hydrophilic/hydrophobic porous polymers of the present invention. U.S. Pat. Nos. 5,141,806 and 5,215,790 are hereby incorporated herein in their entirety by reference. Particulated porous polymer substrates are treated in the drop tower. The sidearm reactor is used when uniform treatment of relatively larger solid forms of the porous polymer substrate is desired, e.g. the treatment of a sheet or block to a uniform depth across one exterior surface.

Porous and non-porous compatibilized articles made by the method of the invention find widespread use in biotechnical and biomedical application. By "biotechnical" it is understood to mean application to vitro processes. Examples of in vitro processes include manufacturing and purifying biocompounds such as lipids, complex carbohydrates, proteins and nucleic acids; preparing pharmaceutical chemicals used as drugs, drug intermediates, and the like; and cell culturing processes for drug manufacture, preparing organisms having altered genes, prostheses manufacture, and the like. "Biomedical" generally refers to vivo process application, i.e. extended contact with ongoing life processes.

The extent of compatibilization depends on the given application. Close compatibilization may duplicate the cell linings at the location of transplant. Lesser compatibilization may only require water wettability of a hydrophilic surface. Intermediate compatibilization may mimic a biologic substrate to a greater or lesser extent, enhance adsorption of biologic compounds such as albumin previously mentioned or prevent adhesion such as that of platelets to reduce unwanted clotting also previously mentioned. It is understood that a compatibilized substrate for an in vivo application is less likely to cause localized damage and/or irritation in an organism. An implant having compatibilized surfaces can last longer and is generally less likely to be rejected by the organism. A compatibilized substrate for an in vitro process will enhance the application and/or yield of the biotechnical process.

Representative examples of biomedical applications include contact lenses, dressings for enhancing the healing of skin, membranes for blood dialysis, prostheses for the vascular and skeletal system, artificial organs, implants for reconstructive and cosmetic surgery, implants for fighting disease, implants for regulating biological systems, implants for providing structural support for directing vascularization wherein the support frame implant is later removed, and the like.

Examples of biotechnical applications include gas and liquid separation membranes in the manufacture and/or purification of pharmaceutical compounds, chromatographic resins, improved cell culturing membranes and petri dishes, membranes for enhancing an evaluation rate of malignant cell growth, vascular conduits for microgravity cell culturing, diagnostic membranes for immune response testing, and the like.

Serological techniques such as enzyme-linked immunosorbent assay (ELISA) for determining the presence of antigens are enhanced by using a membrane wherein one surface is made hydrophilic by the method of the present invention. Successive sera liquids used by ELISA test can be easily drawn through the membrane into an absorbent cotton or tissue paper using surface energy forces, thus avoiding undesirable washing steps which would otherwise be necessary. In such a manner, waste liquids can be more easily limited and confined. The hydrophobic side of the membrane is preferably used for the test reagent side and the hydrophilic side is set adjacent the absorbent paper to draw away the reagents and other test fluids from the test site. The ELISA test can be conducted using the modified membrane in either the "sandwich" method or the indirect method. The methods of the ELISA test are well known in the art.

Cell culturing techniques can be enhanced using polymeric membranes modified by the method of the present invention, especially for culturing cells that require anchorage to a hydrophilic surface to grow. Modified semipermeable membranes having various hydrophilic/hydrophobic surface patterns can be made by masking the membrane before exposure to the atomic oxygen. Such modified membranes can be used as partitions in cell cultures. As one example, the membranes may be masked using a checkerboard stencil, and then modified by atomic oxygen treatment to form hydrophilic surface areas separated by hydrophobic boundaries. In a cell culture, each hydrophilic area comprises a separate microculture because cell growth is substantially confined to the hydrophilic area. Therefore, the hydrophilic "squares" typically have an area several times larger than the size of the cell to be grown. Cells cultured on the checkerboard membrane at an average density of about one cell per hydrophilic square or less form microcultures which can be used to greatly reduce the time and amount of materials required, for example, to make malignant cell growth evaluations of cells taken from tissue biopsies. A percentage of malignant growing cells can then be easily determined by observation of the whole.

Typically, tissue biopsy cells are evaluated for cancerous growth by culturing individual cells separately, and then observing the growth after a period of time. To insure no more than one cell per culture, the cells are ordinarily diluted serially using growth media to a concentration of about 0.6–0.8 cells per culture area. The less culture area required to differentiate between the cells, the less time and nutrients that are generally necessary for the evaluation. Typically, the area of the prior art evaluation cultures is about 0.25 $cm^2$.

Cells can be cultured in a vessel partitioned by a semipermeable membrane into compartments. Nutrients and/or products made by the culture may diffuse across the membrane. For example, a cell culture can be grown in a growth medium in a vessel wherein nutrients are self-replenished as used. The vessel is partitioned by a modified membrane of the present invention into dual compartments. The modified membrane has a hydrophobic surface and a hydrophilic surface. In one compartment adjacent the membrane hydrophobic surface, cells are cultured. The other compartment adjacent the membrane hydrophilic surface has growth medium. Nutrient diffusion from the nutrient compartment replenishes nutrients in the cells compartment as they are used.

Bioreactors partitioned by the modified membranes of the present invention as above can polarize the cells and thereby enhance production and separation of secreted biological products. Depending on the cells involved, polarization can occur in due course as cells adhere to a hydrophilic surface on the membrane and/or in response to a concentration gradient set up by a nutrient factor diffusing across the membrane. In either case, the cells define a basal cell wall adhered against the membrane partition and an opposite apical cell wall. The membrane of such bioreactors preferably has a hydrophobic surface adjacent a cell culture compartment except for an isolated hydrophilic area, such as, for example, a line or a strip for cell attachment. The other surface of the membrane adjacent a nutrient compartment can be hydrophobic or hydrophilic. Nutrients from the nutrient compartment diffuse through the membrane by concentration gradient to replenish nutrients used by the cells. Desired products made by the cells secrete through the basal cell wall and diffuse through the membrane partition into the nutrient compartment. In such manner, desired cell products can be recovered without lysing the cells.

The cell or tissue culture flask of the invention is illustrated in several illustrative embodiments in FIGS. 1–4 wherein like parts are referred to by like numerals. The T-flask 10 in FIG. 1 has a generally longitudinal housing 12 with a generally rectangular or other suitable transverse cross-section. A first end 14 is sealed and a second end 16 is provided with a conventional port 18 for gas exchange and media changeout. The growth media is typically less than about 1.5 mm (¹⁄₁₆-in.) deep above a flat porous polymer insert 20 which is generally about 1–5 mm thick, typically about 1.6 mm (¹⁄₁₆-in.) thick. The housing 12 and ends 14, 16 are conventionally polystyrene or polycarbonate, but any suitable materials may be employed. The housing 12 is typically cut to the desired length and the ends 14, 16 and insert 20 are glued or welded (e.g. ultrasonically) in place to fabricate the T-flask.

The insert 20 is generally rectangular corresponding to the dimensions of the flask 10. The insert 20 has porosity which depends on the size of the cells or tissue to be cultured. Generally, the effective pore diameter should exceed the diameter of the cells as attached to the interstitial surface, and preferably the pore diameter is about five times the cell diameter, to allow media diffusion through the interconnected pores and around the attached cells. The use of the interstitial surface as an attachment surface for the cells greatly increases the surface area for cell attachment and growth, and thus greatly increases the density of the cells being cultured in a given flask volume or surface area.

The pore surface chemistry can be modified as desired to enhance cellular attachment, protein adhesion, etc. as described above. The insert 20 can be treated, for example, by exposure to atomic oxygen or amino radicals to render the interstitial surface hydrophilic to enhance cellular adhesion. If desired, proteins are coupled to the hydrophilic interstitial surface to further enhance cellular adhesion, substantially as described herein. Also, the pore surfaces can be modified by coupling with a peptide ligand for selectively binding proteins expressed by the cells as a product, to facilitate recovery of the protein product directly from the insert 20. In this manner, the media and the cells can be washed from the insert 20, and the protein product can be efficiently cleaved from the pore surfaces without the need for purifying the protein from the growth media.

The pore surfaces in the insert 20 can also have the distributed pore chemistry (DPC) as described above. In this embodiment, the insert 20 is modified to a depth from an upper exterior surface for cell attachment and growth. Below the cell growth modification layer, e.g. to a lower exterior surface, the pore surfaces are modified for selective retention of a protein product secreted by the cells, for example, by filling the pores with a lightly crosslinked affinity gel or a lightly crosslinked dextron, agarose or polyacrylamide gel having attached affinity ligands. The DPC modification is obtained, for example, by atomic oxygen/amino radical exposure of the insert 20 to an initial depth (or through the complete depth), coupling of the gel material to the hydrophilic pore surfaces, removal of the gel materials to a lesser depth by atomic oxygen exposure and derivatizing the resulting hydrophilic gel-free pore surface with any cell adhesion promoters. Crosslinking and affinity ligand coupling of the gel can be effected as intermediate steps in an appropriate sequence or order.

Figure 2:
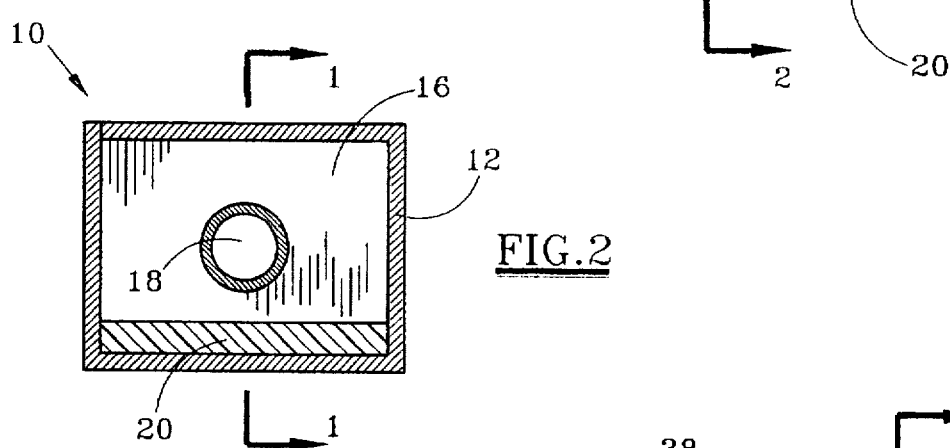
FIG. 2 is a cross-sectional view of the T-flask of FIG. 1 as seen along the lines 2—2.
Figure 3:
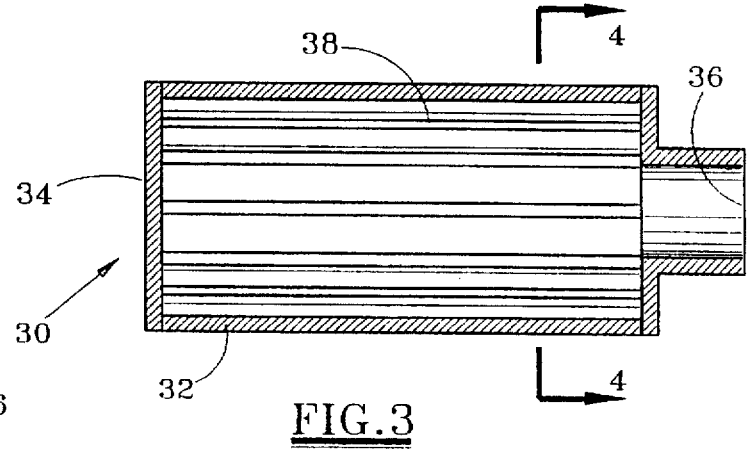
FIG. 3 is a side sectional view of a cell-culturing roller flask according to another embodiment of the invention.
Figure 4:
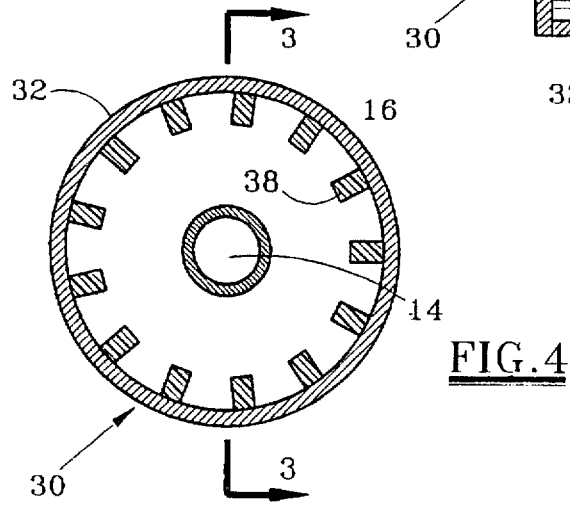
FIG. 4 is a cross-sectional view of the roller flask of FIG. 3 as seen along the lines 4—4.

In a roller bottle embodiment as best seen in FIGS. 3–4, a flask 30 is constructed of a housing 32 and respective first and second ends 34 and 36 as in the T-flask embodiment of FIGS. 1–2. However, the housing 32 is circular in cross-section (see FIG. 4) and is provided with a plurality of porous polymer inserts 38, each of which is modified as described in connection with the insert 20 above.

Each of the inserts 38 is ultrasonically welded or press fit into a respective slot (not shown) on an inside diameter of the housing 32. In use, the roller bottle flask 30 is continuously turned along its axis to alternately immerse and expose each insert 38 so that the cells culturing on the interstitial surfaces thereof continuously receive nutrients and oxygen. Again, as in the embodiment of FIGS. 1–2, the roller bottle of FIGS. 3–4 has markedly increased cell adhesion/growth surfaces as compared to conventional roller bottle designs wherein only a flat interior surface on the inside wall of the flask is available.

The invention is illustrated by the following examples.

EXAMPLE 1

A polytetrafluoroethylene reinforced silicone membrane sold under the tradename SILON by Bio-Med Sciences, Inc. of Bethlehem, Pa. is uniformly treated with atomic oxygen in an atomic oxygen reactor having a specimen holding sidearm. Operating conditions are shown in Table 1. The membrane initially has a hydrophobic surface which after treatment acquires hydrophilic hydroxyl functionality as follows: before after

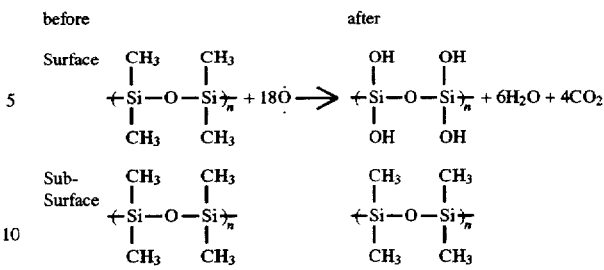

TABLE 1

| pressure (Pa) | 27 |
|---|---|
| temp (°K.) | 298 |
| gas mixture | 10% $O_2$ in Ar |
| C(z) (AO/cm$^3$) | $4 \times 10^{14}$ |

EXAMPLE 2

The membrane of Example 1 is reacted with a silane coupling agent to graft glycidyl functionality to the substrate surface. The grafting reaction proceeds as follows:

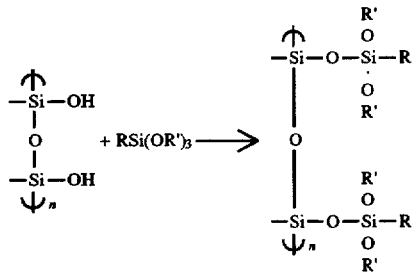

wherein R and R' are as previously defined.

3-Glycidylpropyltrismethoxysilane obtainable from Huls-Petrarch (item G6772) is dissolved in an ethanol/water solution (95 wt % ethanol) to make a 1 wt % solution of the glycidyl compound. The pH of the solution is adjusted to between about 4.5–5.5 with sodium acetate. The membrane from Example 1 is placed into the solution for 1–2 minutes then removed and rinsed with ethanol. After drying for 5–10 min at 110° C. or for 2.5 hrs in a desiccator, the membrane is used for further reaction.

EXAMPLES 3–4

Compatibilizing phosphorylcholine functionality is grafted to the surface of the membranes of Example 2 to mimic a cell membrane.

The membrane of Example 2 is stirred in a 40° C. water solution of ethyleneglycophosphorylcholine for 16 hours. The pH of the reaction medium is 4.5 to 6. The reaction is as follows:

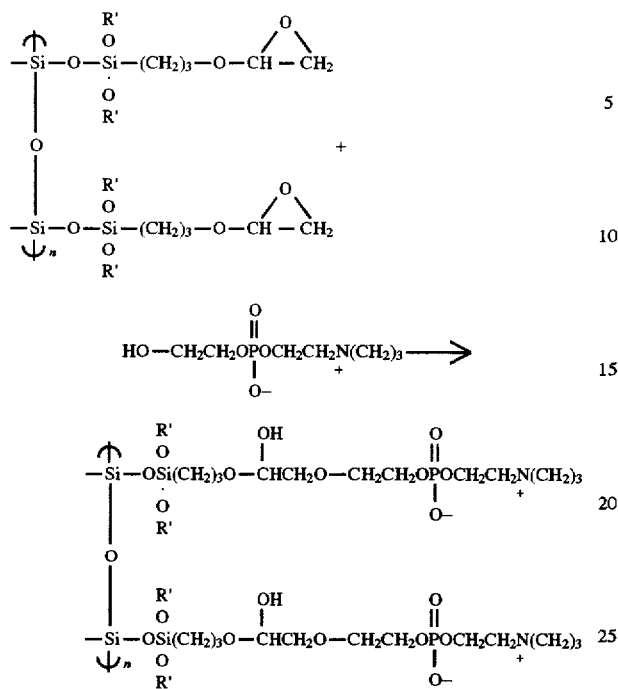

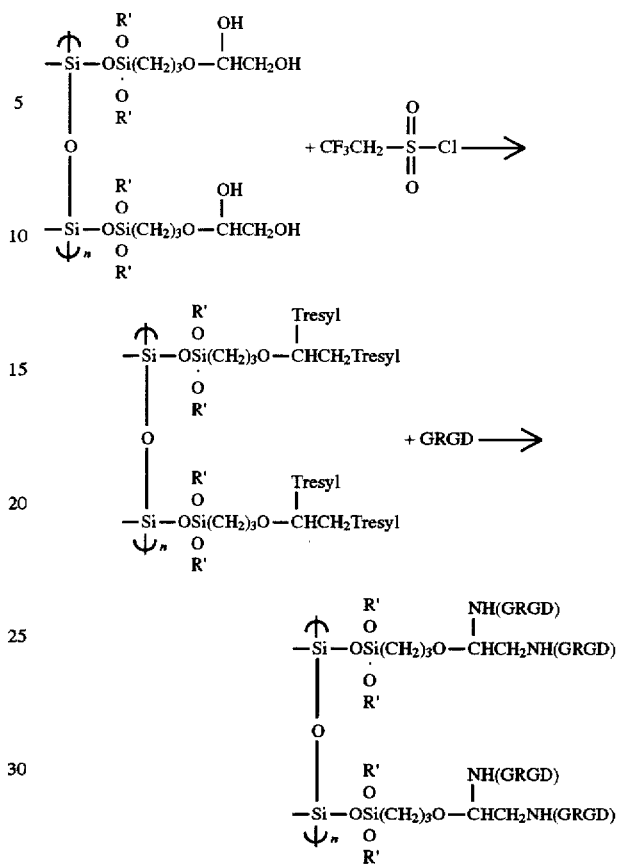

As an alternative example, the membrane of Example 1 is coupled to the ethyleneglycophosphorylcholine using dichlorodimethylsilane. First, the phosphorylcholine is reacted at with the dichlorodimethylsilane in anhydrous tetrahydrofuran (THF) using excess silane for 1 hr at 25° C. to prepare a chlorosilane/phosphorylcholine intermediate. Next, the intermediate product is recovered by evaporating the solvent and excess unreacted silane. The intermediate is then reacted with the Example 1 membrane in dry THF also at 25° C. for 16 hrs with stirring to complete the graft reaction.

EXAMPLE 5

In this reaction, a compatibilizing polymer segment is grafted to the surface glycidyl functionality of the membrane of Example 2.

A poly(vinyl alcohol) segment is grafted to the membrane by reaction in water at 25° C. for 16 hrs with stirring. Reaction pH is 4.5–5.5 Further details regarding the optimized surface loading (# of grafts) and molecular weight distribution of the polymer with respect to a particular application may be found in the article by Y. Ikada mentioned previously.

EXAMPLE 6

A tetrapeptide glycine-arginine-glycine-asparagine (GRGD) containing the cell adhesion sequence arginine-glycine-asparagine (RGD) is grafted to the surface of the membrane of Example 2. Tresyl chloride is used as a second coupling agent as follows:

The glycidyl functionalized membrane from Example 2 is initially hydrolyzed in dilute acid (pH of about 2) by stirring for 2 hrs at 25° C. The hydrolyzed glycidyl groups are reacted with tresyl chloride in dry ether. The membrane is contacted with a 1.0 wt % ether solution of the tresyl chloride at 25° C. for 15 min then rinsed with 0.2M bicarbonate buffer solution having a pH of 10. In fresh buffer solution, the tresyl chloride functionalized membrane is reacted with the peptide for 20 hrs at 25° C. The peptide sequence is attached at the terminal amino functionality on the glycine unit.

EXAMPLE 7

In the following example, a vascular prosthesis is initially made according to Example 6 except that the SILON substrate has the form of a small bore tube. In the atomic oxygen treating first step, the outside surface of the tube is made hydrophilic to ½ of the wall thickness. Arterial endothelial cells are cultured on the treated surface to form a closely compatibilized article which is suitable for implant into a patient suffering advanced arteriosclerosis.

EXAMPLE 8

A vascular prosthesis is made according to Example 7 except that the tubular silicone substrate has a microporous form made by a replamineform casting procedure described in Stimpson above which is hereby incorporated herein by reference.

EXAMPLE 9

In the following example, an ELISA serological immune diagnostic technique is conducted using a 2.5 cm diameter, 100 mm thick SILON membrane treated with a uniform dose of atomic oxygen according to the procedure of Example 1 so that one side is hydrophilic and the other remains hydrophobic. The direct sandwich method is used.

The membrane is placed hydrophilic side down on a glass petri dish and a drop of antiserum containing a polyclonal anti-IgG antibody obtained as a 1 ml concentration from Sigma Corp. of St. Louis is placed on the membrane and allowed to dry. Next, absorbent tissue paper is placed under the membrane hydrophilic side and a drop of a test serum containing complementary antigens is placed over the antibodies. The complementary antigens adhere to the anti-IgG antibodies and excess fluid is absorbed through the membrane into the tissue paper. Using fresh absorbent tissue paper in a fresh petri dish, a second drop of antiserum containing 1 part complementary anti-IgG antibodies per 2000 parts water is placed over the antibody-antigen combination except that these second antibodies are conjugated to an enzyme alkaline phosphatase. Adherence of these additional antibodies to the antigens mark the antigens with the enzyme. Excess liquids diffuse through the membrane and are absorbed by the paper. Using fresh tissue paper in a fresh petri dish, a drop of phosphatase-reactive chromagen is placed over the membrane "sandwich." Since phosphatase marked antigens are present, a black chromagen-phosphatase product forms. Excess fluid is drawn through the membrane and is absorbed leaving the black colored "sandwich." The modified membrane allows waste liquids to be absorbed away from the test area for easy disposal.

EXAMPLE 10

In the following example, time required to differentiate the growth rate of normal cells from malignant cells in a tissue biopsy is determined using a hydrophilic modified membrane of the present invention. The membrane has a surface wherein a plurality of hydrophilic surface areas are separated by a hydrophobic boundary so that each hydrophilic area is an isolated microculture.

The test is undertaken using a 2.5 cm diameter, 100 mm thick SILON membrane exposed to a uniform dosage of atomic oxygen according to Example 1, except that the membrane is masked during the atomic oxygen treatment. The mask gives the membrane a surface feature wherein hydrophilic areas of about 200 mm$^2$ are bounded by similarly sized hydrophobic regions in a checkerboard manner. The treated membrane is placed in a petri dish. The biopsy cells are serially diluted with cell culture media so that there will be about 0.7 cells per 200 mm$^2$ membrane area in the culture and the growth solution containing the cells is then added to the dish.

After one week, observation of the growth area under a microscope indicates that malignancy growth evaluation may be made in one tenth the time ordinarily required using 0.25 cm$^2$ size cultures in the prior art methods. Likewise, only one tenth the amount of culture materials is required.

EXAMPLE 11

In the following example, a modified membrane of the present invention is used to separate a cultured product comprising cell growth differentiation factors from the cells without lysis.

Normal human primary cells taken from a surgical section are cultured in a petri dish having a modified membrane partition. $CO_2$ incubation conditions are used to produce cell growth differentiation factors wherein the cells are polarized by a 2.5 cm$^2$ SILON diffusion membrane which is 100 mm thick. The membrane is treated on both sides with a uniform dose of atomic oxygen according to the procedure of Example 1. One membrane side is hydrophilic and the other remains hydrophobic except for a horizontal hydrophilic line made by masking the treated surface. In the culture, the cells are added to the partition side having the linear hydrophilic area bounded by the hydrophobic area and growth media is added to the other side of the membrane having the hydrophilic surface. The cells polarize as a matter of course upon adherence to the hydrophilic "line" so that a distinct basal cell wall is formed adhered to the membrane as well as an opposite apical cell wall. In the course of the culture, nutrients diffuse across the membrane to replenish the cell growth media and the cell growth differentiation factors produced by the cultured cells are secreted by the basal cell wall and migrate through the membrane partition. After 30 days, the confluency in the opposite compartment is greater than 10 picomoles of the growth differentiation factors.

EXAMPLE 12

In the following example, a modified membrane can be used to allow continual replenishment of nutrients to a cell culture. A petri dish culture is partitioned by modified membrane as described in Example 11 except that the SILON membrane is treated with atomic oxygen so that one side is hydrophilic and the other remains hydrophobic. The hydrophilic side forms the nutrient compartment and the cells are cultured in growth media adjacent the hydrophobic side. As nutrients in the growth medium are used by the cells, replenishing nutrients diffuse from the nutrient compartment to the cells compartment through the membrane.

EXAMPLE 13

Discs of porous and nonporous high density polyethylene (HDPE) were treated with atomic oxygen to evaluate mass loss and the development of hydrophilicity. The porous polyethylene discs were cut from 1.6 mm ($\frac{1}{16}$-in.) thick specimens obtained from Porex Technologies and had coarse, medium and fine pores with respective nominal pore diameters of about 250 µm, 49–90 µm and 10–20 µm. The nonporous HDPE was obtained in the form of a 0.025 mm (1 mil) film. The discs had a diameter of about 19 mm (0.75 in.) and were cleaned by rinsing in a mixture of 1,1,1-trichloroethylene and ethanol and drying in a vacuum overnight.

Duplicate sets of the discs were placed in the sidearm reactor of Example 1 and exposed to an atomic oxygen concentration of $5 \times 10^{14}$/cm$^3$. The weight of each disc was recorded at periodic intervals over a total exposure time of 12–15 hours to monitor mass loss. The results are presented in Table 2. In addition, scanning electron micrographs (SEM) of discs exposed to $3.6 \times 10^{14}$/cm$^3$ atomic oxygen atoms in the sidearm reactor for 166.25 hours were taken for comparison to unexposed material. As seen from the data in Table 2, the rate of mass loss varied according to material pore size, i.e. the larger the pore diameter, the greater the mass loss rate. Apparently, the mass loss rate depends mostly on the amount of surface area available for reaction, and not on diffusion. Estimates of the effective surface area of the discs calculated from the loss rate relative to the nonporous HDPE were corroborated from surface area estimates by SEM. The SEM also showed rounding of particles in the coarse pores and visible pitting in the medium and fine pores, with changes occurring uniformly across the thickness of the discs.

Discs were similarly exposed to $5 \times 10^{14}$/cm$^3$ atomic oxygen atoms in the sidearm reactor for periods of time ranging from three seconds to ten minutes to characterize development of hydrophilicity as reflected in the amount of water uptake of the exposed samples. An amount of water sufficient to wet the hydrophilic portion was dropped onto the surface of each disc, and any excess was removed by pipet. The increase in mass due to water uptake was recorded, and the results based on an average of three specimens are presented in Table 3.

TABLE 2

| Time (hours) | Sample Weight (mg) | | | |
|---|---|---|---|---|
| | Disc #1 | Disc #2 | Disc #1 | Disc #2 |
| | HDPE Sheet (1 mil) | | POREX, Medium (49–90 µm) | |
| 0.0000 | 6.8223 | 6.7433 | 226.8562 | 229.1452 |
| 1.833 | 6.4403 | 6.3288 | 225.2864 | 227.5929 |
| 4.0667 | 6.1962 | 6.0763 | 224.4133 | 226.7565 |
| 5.8834 | 5.9684 | 5.8701 | 223.6999 | 226.0678 |
| 7.8001 | 5.7616 | 5.6614 | 223.0172 | 225.3709 |
| 9.7834 | 5.5604 | 5.4508 | 222.3613 | 224.6970 |
| 11.7834 | 5.3590 | 5.2480 | 221.6863 | 223.9940 |
| 14.2834 | 5.1219 | 5.0195 | 220.9277 | 223.2801 |
| | POREX, Fine (10–20 µm) | | POREX, Coarse (250 µm) | |
| 0.0000 | 254.0969 | 253.5941 | 451.5491 | 454.2949 |
| 1.6167 | 253.0543 | 252.7013 | 450.7072 | 453.0781 |
| 3.6167 | 252.4069 | 252.0329 | 449.8757 | 451.7606 |
| 5.6167 | 251.7920 | 251.4103 | 449.2417 | 451.1571 |
| 7.1000 | 251.2774 | 250.9041 | 448.5435 | 450.6771 |
| 9.1000 | 250.5556 | 250.1976 | 447.8187 | 449.7215 |
| 11.1167 | 249.9119 | 249.5267 | 446.7887 | 449.0990 |
| 12.8500 | 249.3742 | 248.9901 | 445.5790 | 448.0119 |

As seen from these data, the amount of water uptake increased linearly until the saturation level was reached. The development of hydrophilicity clearly occurred prior to observation of any mass loss, and appeared to be dependent on the rate of diffusion of the atomic oxygen through the porous solid. As the pore size increased, the diffusion rate also increased. Also, dyeing of the specimens using a water soluble dye showed that a distinct reaction front progressed through the porous material. The partially hydrophilicized samples had a distributed pore chemistry, the portion ahead of the reaction front remaining hydrophobic while the portion behind the reaction front was hydrophilic.

TABLE 3

| POREX, Fine (10–20 µm) | | POREX Medium (49–90 µm) | | POREX, Coarse (250 µm) | |
|---|---|---|---|---|---|
| Time Exposed (sec) | Water Absorbed (% of disc wt.) | Time Exposed (sec) | Water Absorbed (% of disc wt.) | Time Exposed (sec) | Water Absorbed (% of disc wt.) |
| 5 | 1.9 | 3 | 5.2 | 2 | 4.6 |
| 10 | 8.4 | 5 | 6.7 | 4 | 14.0 |
| 15 | 10.4 | 10 | 12.1 | 6 | 17.3 |
| 20 | 11.6 | 10 | 12.7 | 10 | 25.8 |
| 30 | 14.0 | 15 | 18.9 | 15 | 36.5 |
| 40 | 18.0 | 20 | 18.9 | 15 | 36.5 |
| 50 | 20.1 | 30 | 34.0 | 22 | 47.3 |
| 70 | 23.2 | 40 | 41.8 | 40 | 53.4 |
| 90 | 24.3 | 60 | 48.0 | 60 | 54.1 |
| 120 | 32.9 | 90 | 64.8 | 90 | 52.6 |
| 180 | 47.0 | 120 | 68.0 | | |
| 300 | 55.7 | 150 | 74.3 | | |
| 600 | 65.9 | 180 | 75.0 | | |
| 700 | 65.2 | 210 | 79.5 | | |
| | | 240 | 82.8 | | |

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

I claim:

1. A distributed pore chemistry solid, comprising:
   an exterior surface;
   an interstitial surface comprising interconnected pores having an effective pore diameter up to about 2000 microns formed in an organic polymer opening to the exterior surface; and
   a distributed chemistry of the pores including adjacent hydrophobic and hydrophilic regions;
   wherein the pores in the regions are interconnected at a boundary separating the adjacent regions and the adjacent regions have about the same void fraction;
   wherein the hydrophilic region is essentially free of leachable surfactant.

2. The distributed pore chemistry solid of claim 1, wherein the polymer has an effective pore diameter of at least about 0.01 microns.

3. The distributed pore chemistry solid of claim 1, wherein the polymer has an effective pore diameter of at least about 1 micron.

4. The distributed pore chemistry solid of claim 1, wherein the polymer has an effective pore diameter from about 10 to about 2000 microns.

5. The distributed pore chemistry solid of claim 1, wherein the polymer is a sintered polyolefin or a drawn-film polyolefin.

6. The distributed pore chemistry solid of claim 5, wherein the polyolefin is selected from the group consisting of low density polyethylene, high density polyethylene and polypropylene.

7. The distributed pore chemistry solid of claim 1, obtained by exposing at least a portion of the exterior surface of a hydrophobic polymer substrate to an oxidizing or reducing gas, containing an oxidizing or reducing species selected from atomic oxygen, hydroxyl and amino radicals, at conditions and for a period of time effective to hydrophilicize a portion of the interstitial surface to form the hydrophilic region.

8. The distributed pore chemistry solid of claim 7, wherein the polymer substrate is reactive with the oxidizing or reducing gas such that the substrate would ultimately experience severe mass loss in the presence of the gas, and wherein the hydrophilic region formed by the exposure to the oxidizing or reducing gas has a mass loss less than about one percent of the region before said exposure.

9. The distributed pore chemistry solid of claim 1, prepared by the method comprising the steps of:
   exposing the exterior surface to an oxidizing or reducing gas, containing an oxidizing or reducing species selected from atomic oxygen, hydroxyl and amino radicals, at conditions and for a time effective to hydrophilicize the interstitial surface of said polymer; and
   recovering the polymer having a hydrophilic interstitial surface to a depth spaced from said exterior surface.

10. The distributed pore chemistry solid of claim 9, wherein the polymer has a rate of mass loss from the interstitial surface exposed to the oxidizing or reducing species substantially less than a rate of hydrophilicization.

11. The distributed pore chemistry solid of claim 10, the method of preparation comprising the step of precoating the interstitial surface with an organosiloxane that forms a silicon oxide coating during said exposure to the oxidizing gas to inhibit the mass loss from the interstitial surface.

12. The distributed pore chemistry solid of claim 10, wherein said exposure is of limited duration to form a distinct reaction front behind which the interstitial surface is hydrophilicized, and in front of which the interstitial surface remains hydrophobic.

13. The distributed pore chemistry solid of claim 12, wherein the polymer comprises sintered polyolefin.

14. The distributed pore chemistry solid of claim 13, wherein the polyolefin is selected from high density polyethylene, low density polyethylene and polypropylene.

15. The distributed pore chemistry solid of claim 12, wherein the polymer has pores interconnected across said reaction front.

16. The distributed pore chemistry solid of claim 12, wherein the polymer has an effective pore diameter from about 10 to about 250 microns.

17. A distributed pore chemistry solid comprising:

an exterior surface;

an interstitial surface comprising interconnected pores having an effective pore diameter up to about 2000 microns formed in a normally hydrophobic organic polymer opening to the exterior surface; and a distributed chemistry of the pores including adjacent hydrophobic and hydrophilic regions;

wherein the pores in the regions are interconnected at a boundary separating the adjacent regions and the adjacent regions have about the same void fraction;

wherein the polymer is reactive with atomic oxygen;

wherein the hydrophilic region is surface modified with oxidizing or reducing species selected from atomic oxygen, hydroxyl and amino radicals.

18. The distributed pore chemistry solid of claim 17, wherein the hydrophilic region is essentially free of leachable surface modification.

19. The distributed pore chemistry solid of claim 17, wherein the polymer has an effective pore diameter of at least 1 micron.

20. The distributed pore chemistry solid of claim 17, wherein the polymer has an effective pore diameter from about 10 to about 2000 microns.

21. The distributed pore chemistry solid of claim 17, wherein the polymer is a sintered polyolefin or a drawn-film polyolefin.

22. The distributed pore chemistry solid of claim 21, wherein the polyolefin is selected from the group consisting of low density polyethylene, high density polyethylene and polypropylene.

23. The distributed pore chemistry solid of claim 17, obtained by exposing at least a portion of the exterior surface of a hydrophobic polymer substrate to an oxidizing or reducing gas, containing an oxidizing or reducing species selected from atomic oxygen, hydroxyl and amino radicals, at conditions and for a period of time effective to hydrophilicize a portion of the interstitial surface to form the hydrophilic region.

24. The distributed pore chemistry solid of claim 23, wherein the polymer substrate is reactive with the oxidizing or reducing gas such that the substrate would ultimately experience severe mass loss in the presence of the gas, and wherein the hydrophilic region formed by the exposure to the oxidizing or reducing gas has a mass loss less than about one percent of the region before said exposure.

25. The distributed pore chemistry solid of claim 17, prepared by the method comprising the steps of:

exposing the exterior surface to an oxidizing or reducing gas, containing an oxidizing or reducing species selected from atomic oxygen, hydroxyl and amino radicals, at conditions and for a time effective to hydrophilicize the interstitial surface of said polymer; and recovering the polymer having a hydrophilic interstitial surface to a depth spaced from said exterior surface.

26. The distributed pore chemistry solid of claim 25, wherein the polymer has a rate of mass loss from the interstitial surface exposed to the oxidizing or reducing species substantially less than a rate of hydrophilicization.

27. The distributed pore chemistry solid of claim 26, the method of preparation comprising the step of precoating the interstitial surface with an organosiloxane that forms a silicon oxide coating during said exposure to the oxidizing gas to inhibit the mass loss from the interstitial surface.

28. The distributed pore chemistry solid of claim 26, wherein said exposure is of limited duration to form a distinct reaction front behind which the interstitial surface is hydrophilicized, and in front of which the interstitial surface remains hydrophobic.

29. The distributed pore chemistry solid of claim 28, wherein the polymer comprises sintered polyolefin.

30. The distributed pore chemistry solid of claim 29, wherein the polyolefin is selected from high density polyethylene, low density polyethylene and polypropylene.

31. The distributed pore chemistry solid of claim 28, wherein the polymer has pores interconnected across said reaction front.

32. The distributed pore chemistry solid of claim 28, wherein the polymer has an effective pore diameter from about 10 to about 250 microns.

33. A porous organic solid, comprising:

an exterior surface;

an interstitial surface comprising interconnected pores formed in a polymer having an effective pore diameter of from about 10 to about 250 microns;

a hydrophobic region of the interstitial surface;

a hydrophilic region of the interstitial surface adjacent the hydrophobic region modified with oxidizing or reducing species selected from atomic oxygen, hydroxyl and amino radicals, essentially free of leachable surface modification, and having a void fraction less than one percent greater than a void fraction of the hydrophobic region; and pores interconnected across a boundary between the hydrophilic and hydrophobic regions.

34. The porous organic solid of claim 33, wherein the polymer is a polyolefin.

35. The porous organic solid of claim 34, wherein the polyolefin is low density polyethylene, high density polyethylene or polypropylene.

36. The porous organic solid of claim 34, wherein the polyolefin is sintered.

37. The porous organic solid of claim 34, wherein the polyolefin is a drawn film.

* * * * *